United States Patent
Evans, Jr.

[11] Patent Number: 5,958,346
[45] Date of Patent: Sep. 28, 1999

[54] POWER-ASSISTED DEODORIZER SYSTEM AND METHOD

[76] Inventor: Bennie L. Evans, Jr., 8108 Riverbend Ct., Fort Washington, Md. 20744-5533

[21] Appl. No.: 08/822,636

[22] Filed: Mar. 25, 1997

Related U.S. Application Data

[60] Provisional application No. 60/032,479, Dec. 9, 1996.

[51] Int. Cl.[6] ........................................ A62B 7/08
[52] U.S. Cl. .............. 422/120; 239/44; 239/45; 239/47; 239/49; 261/DIG. 17; 422/110; 422/123; 422/124
[58] Field of Search .................. 422/1, 4, 5, 120, 422/123, 124, 119, 110; 261/DIG. 17, DIG. 65; 239/45, 49, 47, 44

[56] References Cited

U.S. PATENT DOCUMENTS

| | | | |
|---|---|---|---|
| 4,413,779 | 11/1983 | Santini | 239/95 |
| 5,071,621 | 12/1991 | Tokuhiro et al. | 422/4 |
| 5,102,189 | 4/1992 | Saito et al. | 422/123 |
| 5,302,359 | 4/1994 | Nowatzki | 422/306 |
| 5,591,409 | 1/1997 | Watkins | 422/110 |

*Primary Examiner*—Krisanne Thornton
*Attorney, Agent, or Firm*—Alfred F. Hoyte, Jr.

[57] ABSTRACT

An article deodorizer system and method which is suitable for fixed, mobile, and vehicular mounting and complete interfacing with their air systems at any sites including homes, businesses, airplanes, ships, railcars, automobiles, etc., providing for air improvement by deodorizing selected air streams continuously by effecting the induction of desired interchangeable deodorizing additives into air streams whether conditioned or not improving human conditions. A control system provides for either stand-alone or complete automated operation and complete interfacing with other small and/or supervisory or complex, large control systems.

5 Claims, 7 Drawing Sheets

POWER-ASSISTED DEODORIZER SYSTEM AND METHOD

CROSS REFERENCE TO EARLIER FILED APPLICATIONS

This application claims the benefit of Provisional Application No. 60/032,479 filed on Dec. 9, 1996.

BACKGROUND OF THE INVENTION

1. Field of the Invention

This deodorizer system and method is intended for controlled use in homes, offices, vehicles, airplanes, businesses and the like for active continuous automatic control of air odors found in such as in the conditioned or unconditioned air streams pumped into homes, vehicles, airplanes, work places, business places, and the like, especially when foul odors are inducted into the intake air streams of heating, ventilation, and air-conditioning systems or other air distribution systems where foul odors affect the human conditions.

This deodorizer system will and can be used in combination with existing and future air system configurations, equipment, including heating-ventilation-air conditioning systems and the like used in homes, vehicles, industries, airplanes, rail-cars, subway cars, businesses, and the like. The deodorizer system can be interfaced with current and future air systems as a add on, and/or be incorporated as an integral sub-system by manufacturers of fixed, mobile, vehicular air systems at their factories.

2. The Prior Art

A survey of options and add on's currently available for automated deodorizing air streams did not disclose any similar means, method or system available as a option or add on.

Air deodorizers which are manually placed/operated spray-cans, or passive types are widely available and well known in the art. Air deodorizers of this type must be manually and continuously actuated and/or controlled by an operator and are limited in their effectiveness, continuity, and by costs.

BRIEF SUMMARY OF THE INVENTION

In this invention preselected interchangeable deodorizing fluids are pumped from supply sources to preselected nozzles spraying the preselected deodorizing fluids into foam caps mounted in the air streams of fixed or mobile or vehicular air systems, whether preconditioned or not, to condition by deodorizing and improve the human conditions. It should be understood that the supply sources, pumps, nozzle-foam caps, and control system components can be an integral assembly or mounted remotely from each other and flexibly connected.

In this invention, the deodorizer is powered only at the pump and control unit. It should be understood that the pump and control unit could be powered electrically or by pressurized fluid. The control unit can be remotely mounted and completely interfaced with any other system controls or the deodorizer system can be a stand alone system. The deodorizer system is capable of injecting controlled amounts of any selection of the many types/fragrances/scents of deodorizing fluids with other desired additives, such as anti-freeze or germicials, into ducted air streams continuously and automatedly. It should be understood that the deodorizer could be a automated timed or intermitted or manual operation and/or with selective modes of operation and a preprogrammed or preset selection of times, length of period, and a particular deodorizing fluid for any period of time into any selected air stream(s). It should be understood that any deodorizer system can include an array or arrays of any number of different and interchangeable deodorizing fluids with a preprogrammed or preset time of injection at one or more nozzles for any preprogrammed or preset period of time for any one or more of the arrayed deodorizing fluids all under automated or manual control.

The article deodorizer system and method of this invention is especially useful for improving the air conditions for humans in the many places/sites/vehicles where the human environment includes pumped air which may be conditioned by other methods also or only for ventilation purposes. It should be understood that the term air conditioning includes, but is not limited to, the processes of filtering, adding or removing heat, adding or removing humidity, deodorizing, etc.

DETAILED DESCRIPTION OF THE PREFERRED EMBODIMENTS

Figure 1:
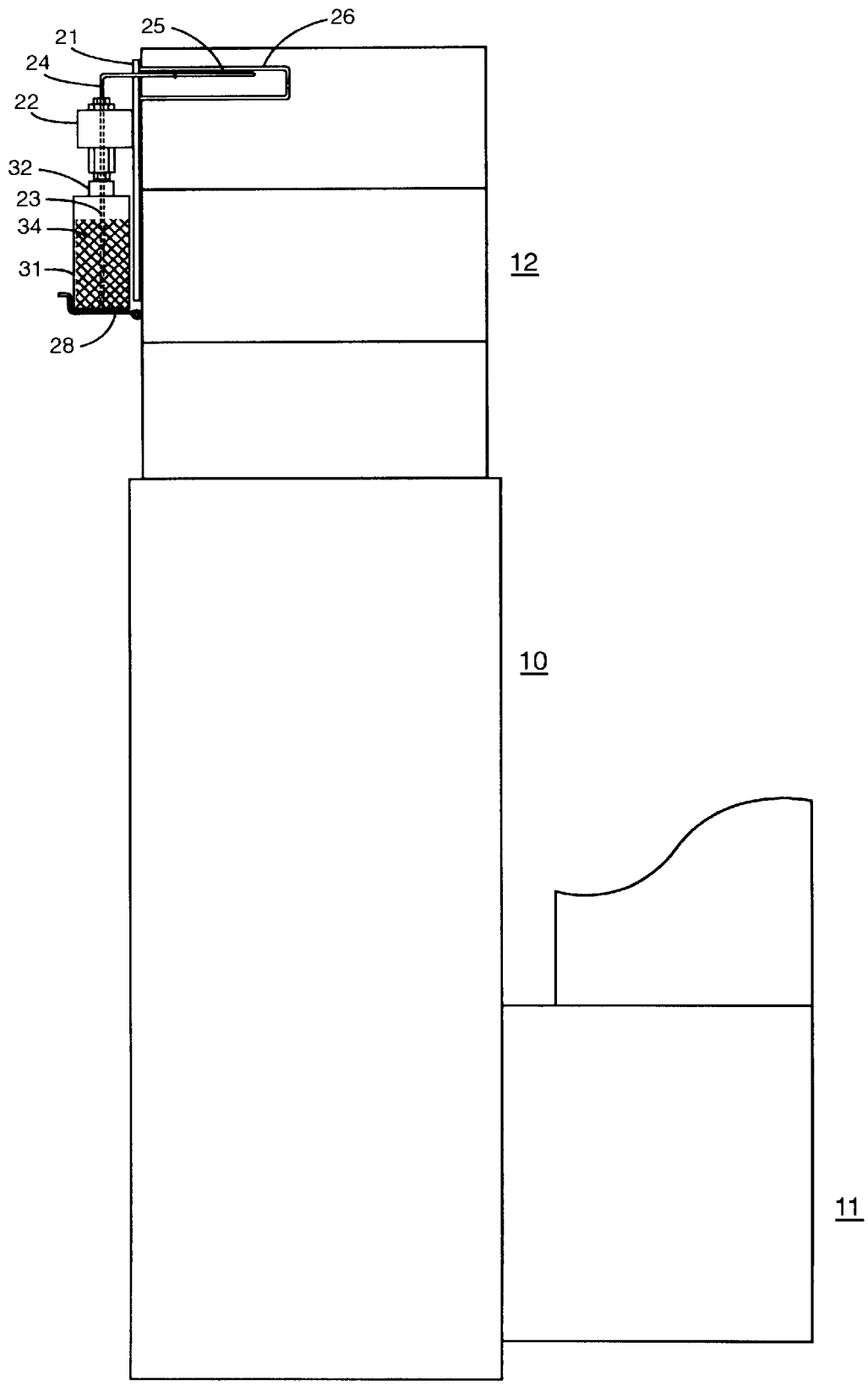
FIG. 1 shows side view of a deodorizer system interfaced with a fixed air system.

In FIG. 1, there is shown a side view of a deodorizer system 40 interfaced with a fixed air conditioning system 10 with the deodorizer assembly 40 mounted on a air duct 12 with selected cross sections. It should be understood that this deodorizer assembly 40 could be attached to any other suitable support whether mobile, vehicular or fixed. It also should be understood that the supply sources 30, pumps 20, nozzle 25-foam caps 26, and control system 60 components can be an integral assembly or mounted remotely from each other and flexibly connected. It also, should be understood that the term air conditioning includes, but is not limited to, the processes of filtering, heating, removing heat, adding or removing humidity, deodorizing, etc. Also shown is a cross section of a air duct 12, a foam cap 26 and a intake air duct 11. When the system is in use, air is pumped from the intake air duct 11 through 10, where the air may be conditioned or not, through output air duct 12 where the air stream impacts the foam cap 26 impregnated with selected deodorizer fluids 34 from supply source bottle 31 by pump 22 through intake pipe 23 through nozzle pipe 24 to nozzle 25 spraying the deodorizing fluids 34 into foam cap 26 which is inside air duct 12 where the air streams impacts the foam cap 26 and flows through and around the foam cap 26 impregnated with deodorizing fluids 34 picking up particles of the deodorizing fluids 34 thus conditioning the air stream continuously while pump 22 is in operation and air streams are moving. It also should be understood that the interchangeable and available deodorizing fluids will include, but not be limited to, the types/fragrances, plus other additives such as anti-freeze or germicidals as desired, as listed in the following Table 1.

TABLE 1

Deodorizing Fluid Types

| Item No. | Fragrances | Color |
| --- | --- | --- |
| 01 | Icey | Clear |
| 02 | Powder-Blue | Clear-Blue |
| 03 | Dusk | Lavender |
| 04 | Oriental-Musk | Orange |
| 05 | Country-Breeze | Yellow |
| 06 | Spicey-Nights | Purple |
| 07 | French-Fumes | Red |
| 08 | Rose-Bud | Pink |
| 09 | Floral-Mist | Green |
| 10 | Hint-o-Gold | Gold |
| 11 | La Cute Peach | Peach |
| 12 | Bubble-Gum | Dark-Pink |
| 13 | Grape-Vine | Deep-Purple |
| 14 | Festive Season | |
| 15 | Rolling Meadows | |
| 16 | Summer Notions | |
| 17 | Summer Desire | |
| 18 | Spring Fever | |
| 19 | The Terrace | |
| 20 | All American | |
| 21 | Fragile Petals | |
| 22 | "2001" | |
| 23 | Apple-crumb | |
| 24 | Automation | |

It should also be understood that the deodorizing fluid pressure system could include a accumulator and control system to provide a closed-loop deodorizing fluid pressures to the nozzle(s) in a selective or preset manner. It also should be understood that the deodorizer operations could be a selection of times, length of period, and a particular deodorizing fluid flowing to a particular nozzle(s) for any period of time at a selected pressure. It should also be understood that any deodorizer system can include an array or arrays of any number of different and interchangeable deodorizing fluid supply sources flexibly connected to one or more pumps with a preprogrammed time of injection at one or more nozzles in one or more selected air streams ducts for any preprogrammed period of time and pressure for any one or more of the arrayed deodorizing fluids all under automated or manual control. Further it should be understood that a deodorizing fluid level sensor connected to a warning/alarm light or/and a buzzer to indicate a low level of deodorizing fluid at any of the supply sources can be part of the control system.

Figure 2:
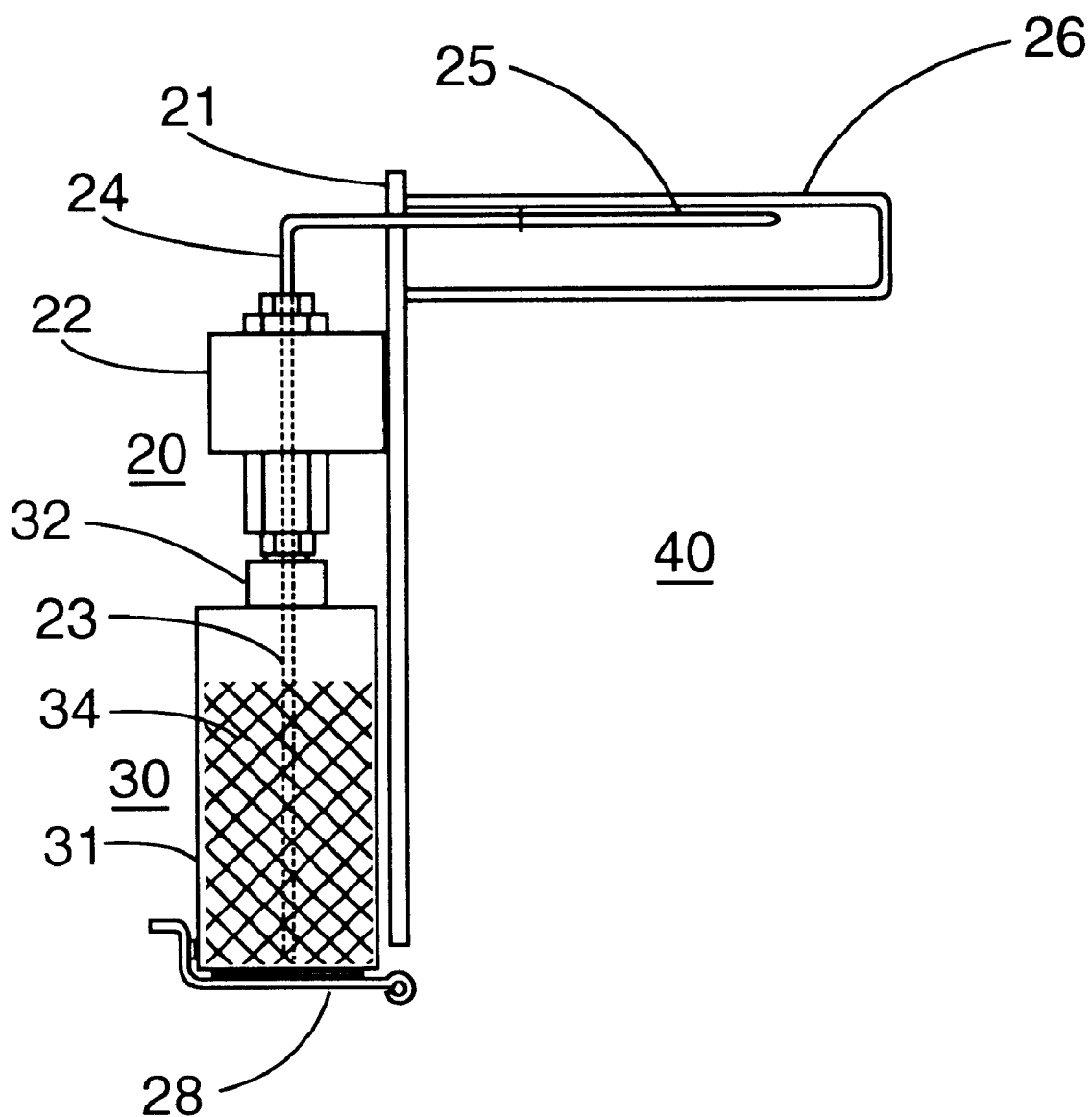
FIG. 2 shows a side view of the fixed deodorizer system.

In FIG. 2 is shown the deodorizer assembly 40 with selected cross-sections comprising a replinishable deodorizing fluid supply source assembly 30, a pumping assembly 20 and a control system 60. The replinishable deodorizing fluid supply source 30 comprising a bottle 31, a bottle cap 32 with a resealable pipe entrance feature, and deodorizing fluid 34. It should be understood that the deodorizing fluid supply source 30 and its components could be of any size/shape/configuration/mounting and arrayed in any number and that the deodorizing fluid supply can be replenished by replacing bottles or by refilling a fixed reservoir using a refill port and/or from a large supply source(s) via a pumping system and a flexibly connection means. The pumping assembly 20 comprising a base plate 21, a pump 22, a intake pipe 23, a nozzle tube 24, a nozzle 25, a foam cap 26, and a spring loaded bottle clamp 28. It should be understood that the deodorizing fluid pumping assembly 20 and its components could be of any size-shape-configuration-mounting and arrayed in any number. The control system 60 at a minimum comprising a relay 61 or valve 62, a on-off switch 63, and a suitable circuit connecting means. The control system 60 at a maximum comprising relays 61 or valves 62, a on-off switch 63, a mode selector 64, a preprogramable timer 65, a preprogramable deodorizing fluid selection means 66, a deodorizing fluid pressure and fluid level sensor system 67, a programmable logic controller or a embedded logic controller 68 and a suitable circuit connecting and interfacing means 69. It should be understood that the control system 60 components could be of any size/shape/configuration/mounting/voltage/pressure and can be a stand-alone system or partially or totally interfaced with other control systems whether a fixed or mobil installation of an air conditioning system.

Figure 3:
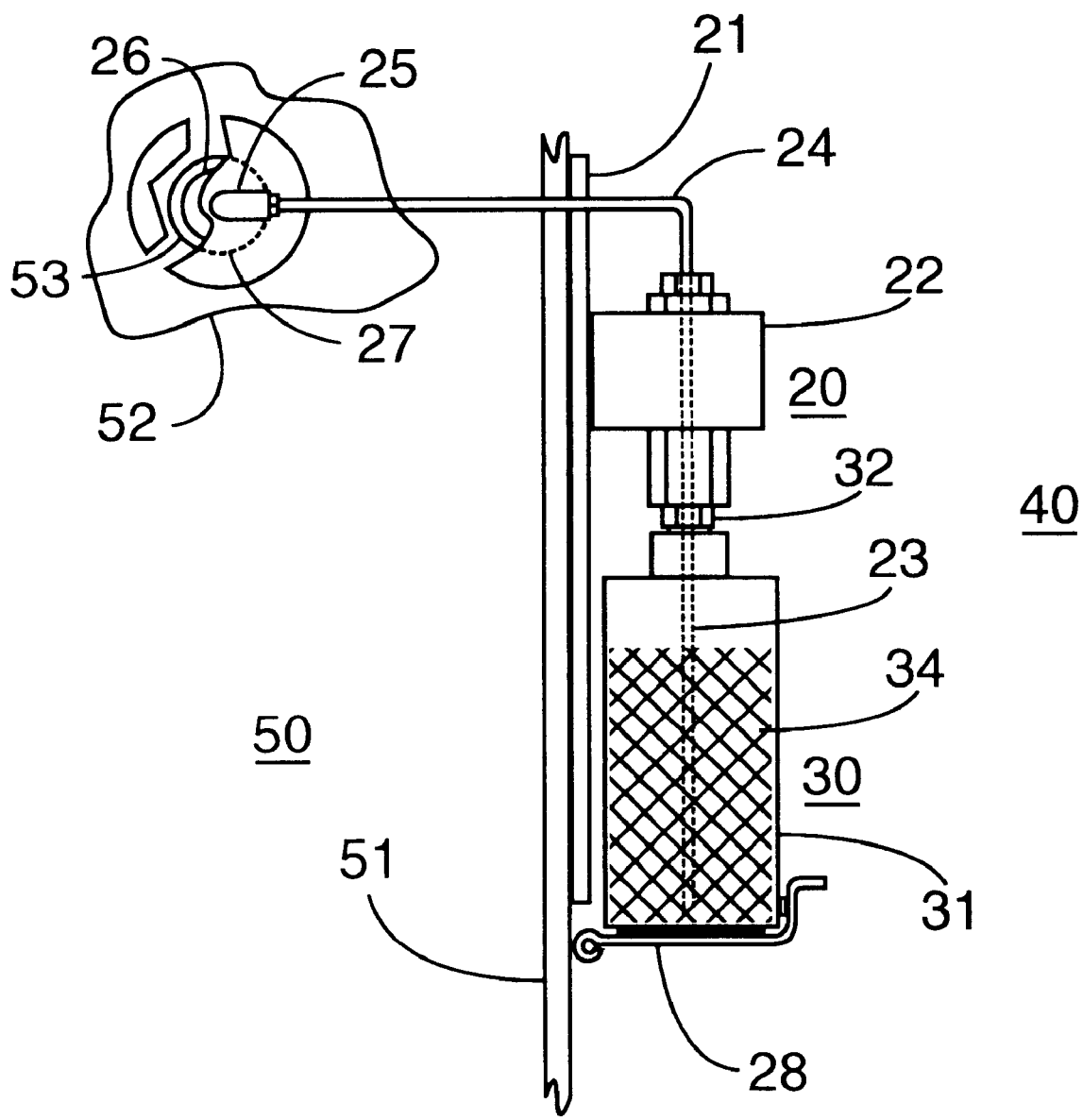
FIG. 3 shows a side view of a mobile deodorizer system interfaced with a vehicular air system.

In FIG. 3 is shown a side view of a mobile vehicular deodorizing system 40 totally interfaced with a vehicular air system 50, including most of the components described in detail and shown in FIGS. 1 and 2, showing the baseplate 21 mounted on firewall 51, nozzle pipe 24 connected to output end of pump 22 passing through firewall 51, to nozzle 25 mounted on nozzle plate 27 mounted on air duct 52 where nozzle 25 and foam cap 26 protrudes through and inside air duct via air duct hole 53 into any air streams passing through air duct 52 where when pump 22 is actuated deodorizing fluid 34 is inducted via intake pipe 23 from deodorizing fluid supply bottle 31 and pressurized by pump 22 through nozzle pipe 24 to nozzle 25 emitting spray patterns of deodorizing fluid into and impregnating foam cap 26 where pumped air streams impact the foam cap 26 inducting particles of deodorizing fluid into the air streams providing continuous deodorized air downstream of this point as controlled by control system 60. It should be understood that the control system 60 components could be of any size/shape/configuration/mounting/voltage/pressure and can be a stand-alone system or partially or totally interfaced with other control systems whether a fixed or mobil vehicular installation of an air conditioning system.

Figure 4:
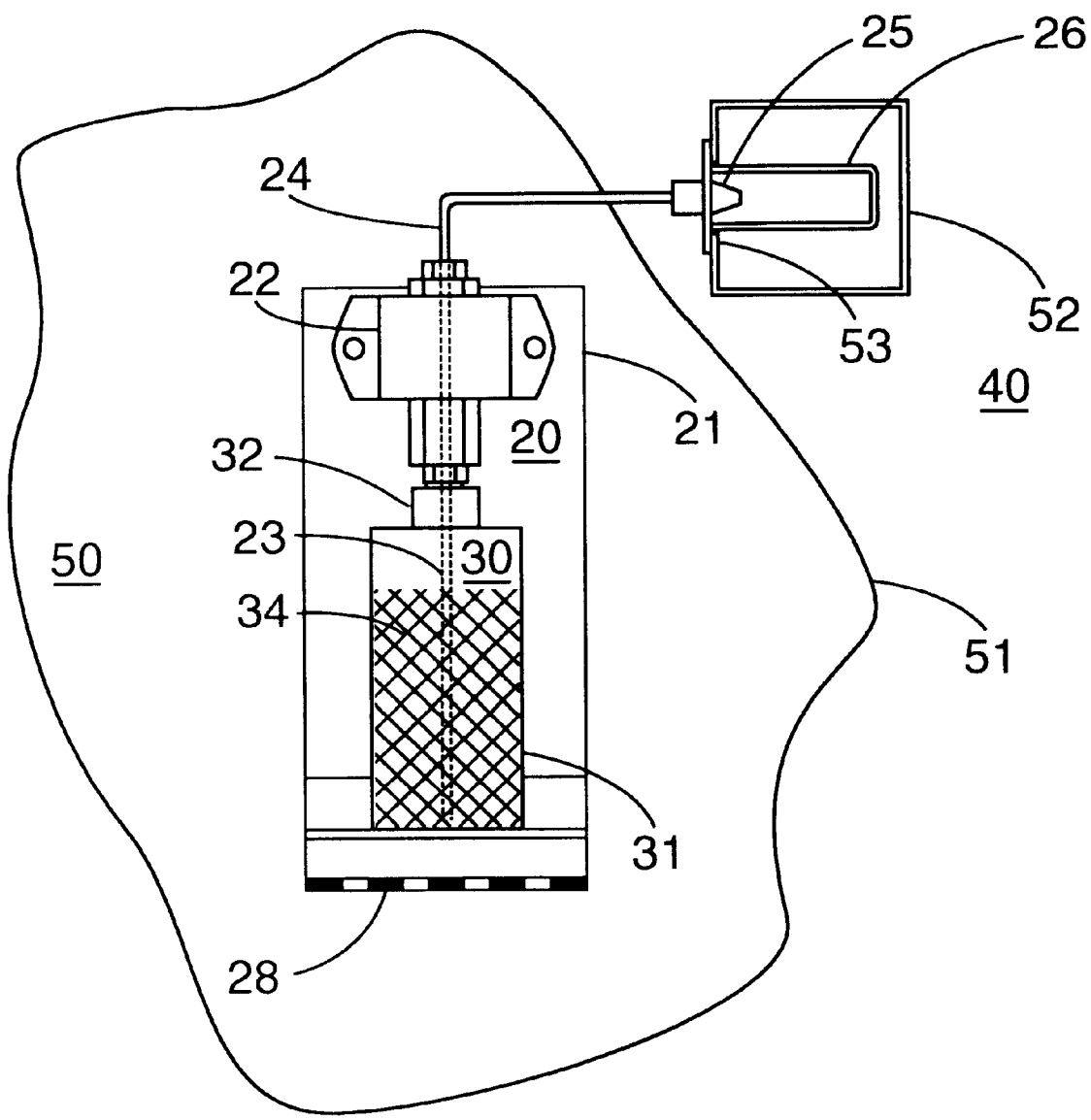
FIG. 4 shows a end view of the mobile deodorizer system interfaced with a vehicular air system.

In FIG. 4 is shown a end view of a mobile vehicular deodorizing system 40 totally interfaced with a vehicular air system 50 including all components described in detail and as shown and described in FIG. 3. It should be understood that the deodorizer system can be named, but not limited to, Anti-Odor, Auto-Fresh, Auto-Scent, Odor-Out, Auto-Mist, Insta-Fresh, etc. . . .

Figure 5:
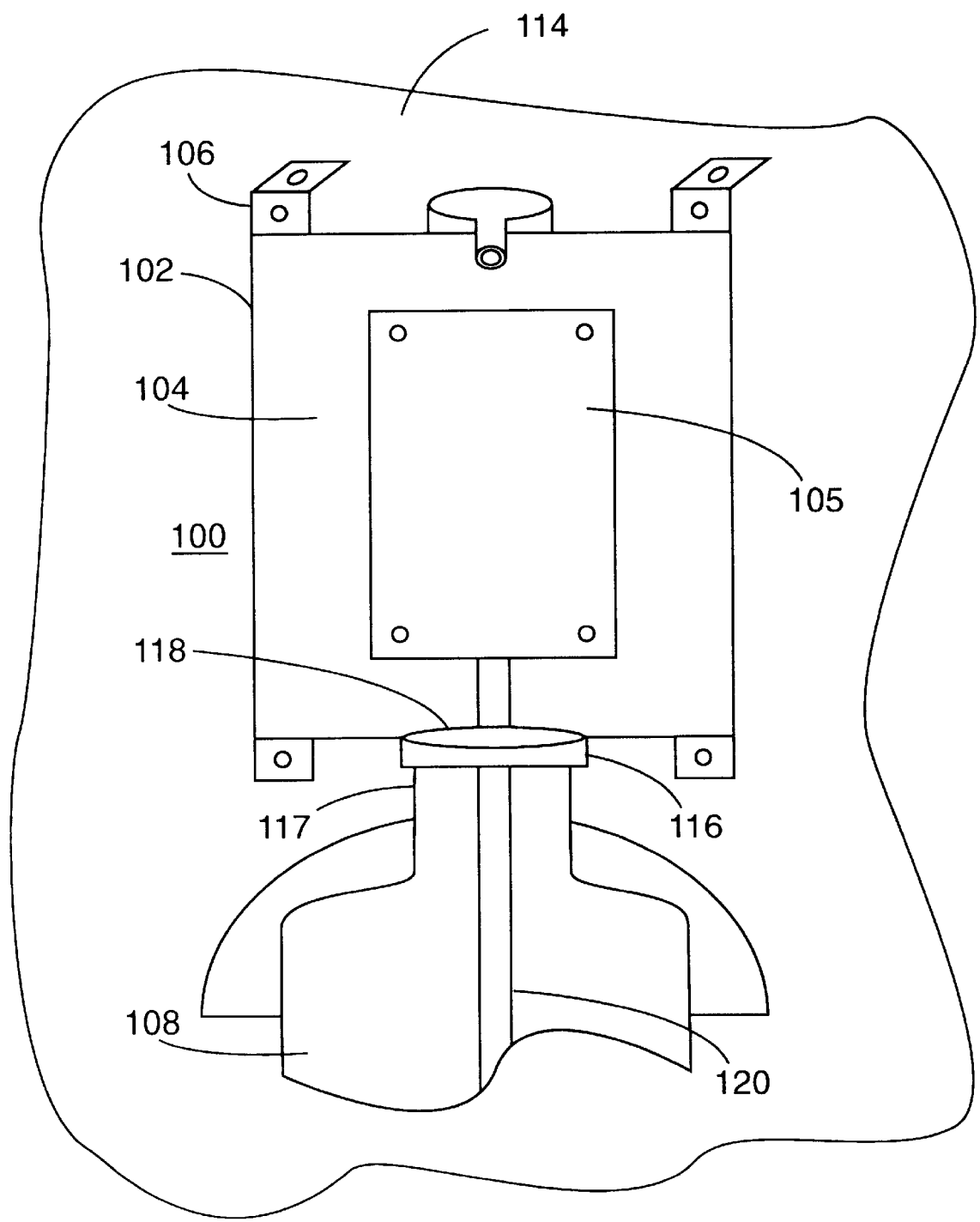
FIG. 5 shows a front view of an alternative embodiment of the mobile deodorizer system.
Figure 6:
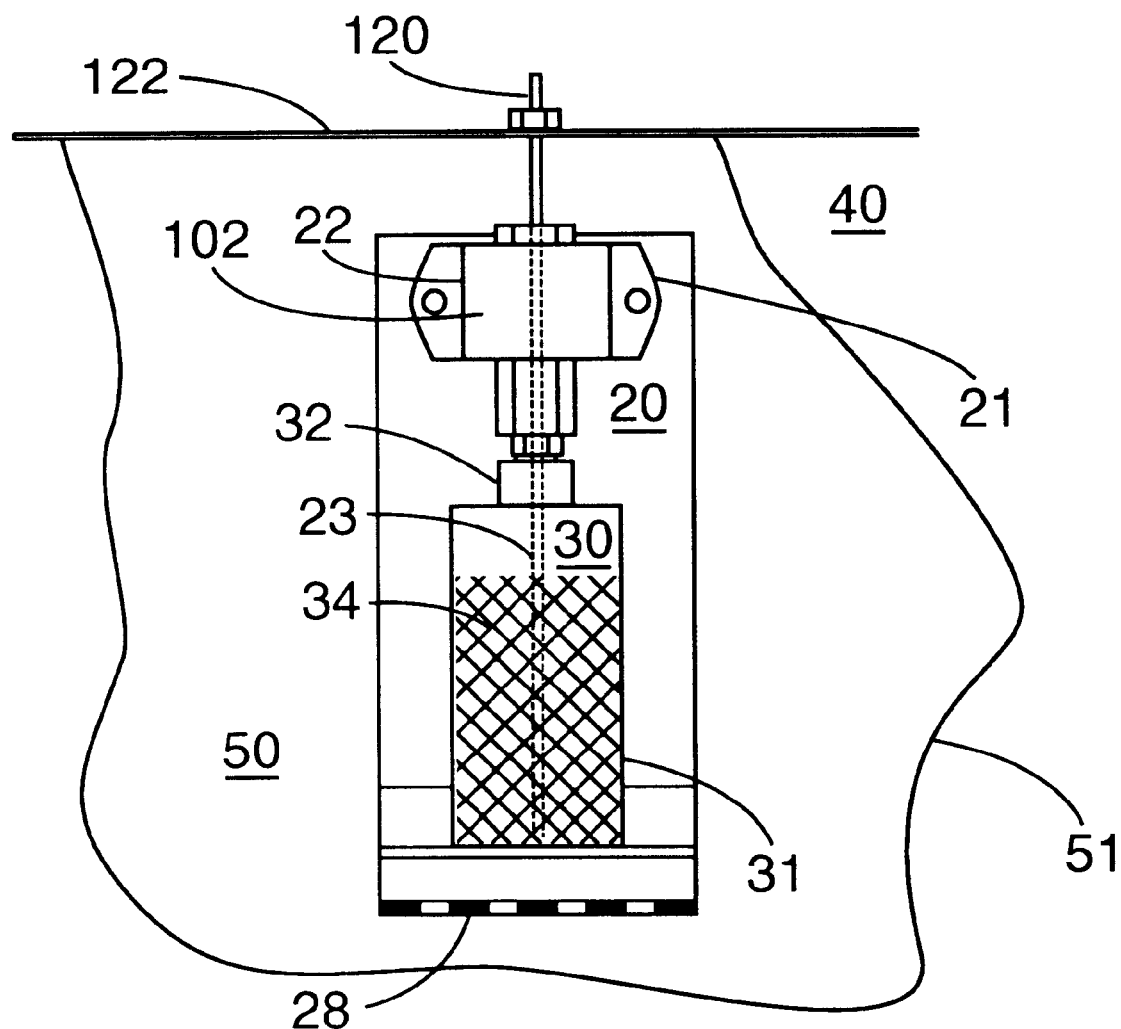
FIG. 6 a front view of the embodiment of FIG. 5 partly in section with the panel cover removed.
Figure 7:
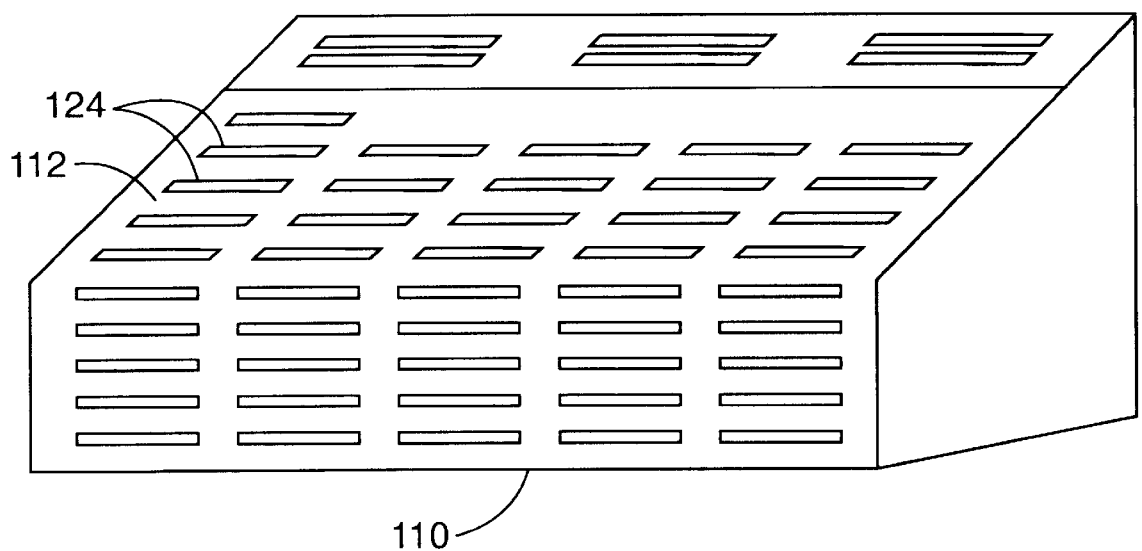
FIG. 7 is a perspective view of the absorbent pad and cover used with the alternative embodiment.

Referring now to FIGS. 5, 6, and 7, an alternative embodiment of the invention generally indicated by the number 100 is shown. This embodiment is not used in conjunction with the cars ventilation system and is preferably mounted on the rear deck and in the trunk of an automobile or other vehicle.

The unit 100 has three basic components, the pump 102 with the associated cover 104 and mounting brackets 106, a fluid container 108, and an absorbent pad 110, and associated vented cover 112.

The pump 102, may be the same as the pump assembly 30, described in connection with the first embodiment. A remotely located switch may be used to actuate the pump 102 as has been previously described. The pump 102 is attached to the interior wall of the cover 104, the cover also including an access panel 105 for allowing access to the pump 102. The cover 104 is used to shield the pump 102 from the elements when the trunk of the vehicle (not shown) is open and also has mounting brackets 106 extending therefrom. The mounting brackets 106 allow for connecting the pump 102 to the rear wall 114 of the trunk or other vertical surface.

Secured to the bottom of the cover 104, is a threaded receptacle 116 for releasably connecting the fluid container 108 which has a threaded end 117. An aperture 118 is formed in the top of the receptacle 116 for a allowing a conduit 120 to pass therethrough.

As can be seen more clearly in FIG. 5, the conduit 120 extends from the interior of the container 108, to the pump 102, and into and through the absorbent pad 110. The conduit 120 preferably terminates with a perforated portion (not shown) which allows for better fluid distribution within said absorbent pad 110. The conduit 120 may be held in place by a clamp or the like to prevent vertical displacement thereof The vented cover 112 has a pair of threaded receptacles (not shown) formed therein which are spaced according to the spacing of the mounting brackets 106 extending from the top of the cover 104. The threaded receptacles are adapted to receive screws (not shown) which extend through the mounting brackets 106, the rear deck 122, and into the receptacles. Thus the entire assembly is supported by the mounting brackets 106 which connect the unit 100 to both the rear wall 114 of the trunk and the rear deck 122 of the vehicle.

The absorbent pad 110 is preferably made of felt or other dense material which has good absorption and moisture retaining characteristics. Fragrance retained in the absorbent pad 110 is released through slots or openings 124 in the vented cover 112. Of course, the absorbent pad 110 has a cylindrical void formed therein for receiving the perforated portion of the conduit 120.

OPERATION

In operation, the control of the deodorizer system can be by an operator while pushing a start button and keeping it depressed for the period of time desired or the operation can be fully automated. The sequence of operations is as follows.

Basic Manual Operation: Replenish deodorizing fluid supply by installing a full bottle of the desired scent or refilling the affixed reservoir, depress and hold start button as desired to spray the deodorizing fluid into the air streams anytime, for any period of time, as desired by the operator.

Fullest, but not limited to, Automated Operation: When a warning light and/or buzzer shows and indicates a low level of deodorizing fluid in one or more of the supply sources, replenish deodorizing fluid supplies in the deodorizing fluid supply array as indicated by installing full bottles of the desired scents or by refilling the affixed reservoirs either manually or via a pumping system with the desired scents in the indicated low-level supply sources, when desired, changes in operations can be accomplished by resetting or by reprogramming of any controls of the modes of operation such as the time of and period of time and at what pressure of injecting which deodorizing fluid into which air duct(s) automatically when the interfaced air system is in operation intermittently or continuous. It should be noted that additional fragrance may be realized in the second embodiment by turning on the defroster and causing warm air to flow over the absorbent pad 110.

What is claimed is:

1. A vehicle mounted deodorizer system for deodorizing air in the interior of said vehicle, said vehicle having a forced air ventilation system including a defroster, said vehicle having a trunk with interior surfaces including a rear wall adjacent to a rear deck, said rear deck having an outer surface facing the interior of said vehicle, comprising in combination:

a selectively interchangeable deodorizing fluid supply source;

a pump assembly operably connected to said deodorizing fluid supply source for drawing fluid therefrom;

said pump assembly and said deodorizing fluid supply source contained within a bracket assembly mounted on said rear wall, an aperture formed in said rear deck with a conduit extending from said deodorizing fluid supply source at one end, into and through said aperture, and terminating at its opposite end in an absorbent pad;

a control system for said deodorizer system, said control system including an operator controlled push-button;

wherein said pumping system pumps deodorizing fluid into and through said conduit spraying said fluid into said absorbent pad.

2. The system of claim 1 wherein said bracket assembly includes shield means integral therewith.

3. The apparatus in accordance with claim 1 wherein the said fluid supply source includes an array of at least two interchangeable supply sources.

4. The apparatus in accordance with claim 1 further wherein said pump system includes an array of at least two separate pumps connected to separate fluid supply sources.

5. The system of claim 1 wherein said absorbent pad is removably attached to the outer surface of said rear deck.

\* \* \* \* \*